United States Patent [19]

Chynoweth

[11] 4,358,537

[45] Nov. 9, 1982

[54] IN SITU BIOLOGICAL BENEFICIATION OF PEAT IN THE PRODUCTION OF HYDROCARBON FUELS

[75] Inventor: David P. Chynoweth, St. Charles, Ill.

[73] Assignee: Institute of Gas Technology, Chicago, Ill.

[21] Appl. No.: 199,680

[22] Filed: Oct. 22, 1980

[51] Int. Cl.$^3$ .............................................. C12P 5/02
[52] U.S. Cl. ................................... 435/162; 435/161; 435/166; 435/167
[58] Field of Search ............... 435/281, 166, 167, 161, 435/162, 163, 164, 165

[56] References Cited

U.S. PATENT DOCUMENTS

| | | | |
|---|---|---|---|
| 1,990,523 | 2/1935 | Buswell et al. | 435/167 |
| 2,742,398 | 4/1956 | Zobell | 435/281 |
| 3,826,308 | 7/1974 | Compere-Whitney | 435/166 |
| 4,187,148 | 2/1980 | Reijonen | 435/167 |
| 4,323,367 | 4/1982 | Ghosh | 435/167 |

Primary Examiner—Raymond N. Jones
Assistant Examiner—John E. Tarcza
Attorney, Agent, or Firm—Thomas W. Speckman

[57] ABSTRACT

This invention relates to a process for in situ biological beneficiation of peat and hydraulic harvesting of organic carbonaceous material from a peat deposit. The process is particularly suitable for production of hydrocarbon fuel from peat wherein peat is contact in situ in a peat deposit with an aqueous solution of hydrolysis promoting agent hydrolyzing organic carbonaceous components of the peat to produce hydrolysis products, passing the hydrolysis products to an active fermentation zone in situ in the peat deposit to produce fermentation products, passing the fermentation products, remaining hydrolysis products and organic carbonaceous materials leached from the peat by the aqueous solution to a biological or chemical process for conversion to hydrocarbon fuel. This process provides peat deposit management while providing beneficiation of the carbonaceous material for improved conversion efficiency by chemical or biological conversion to hydrocarbon liquid or gaseous fuels.

28 Claims, No Drawings 4,358,537

IN SITU BIOLOGICAL BENEFICIATION OF PEAT IN THE PRODUCTION OF HYDROCARBON FUELS

BACKGROUND OF THE INVENTION

1. Field of the Invention

This invention relates to a process for in situ biological beneficiation of peat and hydraulic harvesting of organic carbonaceous material from a peat deposit. The organic carbonaceous material harvested in this fashion is especially suitable in the production of hydrocarbon fuel from peat wherein in situ peat is beneficiated in a peat deposit by contact with aqueous solution comprising a hydrolysis promoting agent hydrolyzing organic carbon components of the peat to produce hydrolysis products, passing the hydrolysis products from the hydrolysis zone to an active fermentation zone in situ in the peat deposit to produce fermentation products, passing the fermentation products, remaining hydrolysis products and carbonaceous materials leached from the peat by the aqueous solution from the peat deposit to an active biological and/or chemical process for conversion to gaseous or liquid hydrocarbon fuel by a process accepting feeds having high water contents. In situ hydrolysis may be achieved by in situ aerobic microorganism activity or by modifying the pH, by lowering it with an acidic material to about 1 to 5 by raising it with a basic material to about 9 to 11. The process of this invention provides high overall efficiency of carbon conversion to useful fuel while providing a more energy efficient process for utilization of the organic carbon components of peat.

Peat is considered to be geologically young coal and has been found extensively throughout the world. European countries and Asian countries have for years extensively used peat as a source of fuel and chemicals. The United States is considered to have the second largest peat resource in the world, but has not used peat commercially as a source of energy. The total energy contained in the United States peat resources is estimated to be equivalent to about 240 billion barrels of oil. Thus, peat is the second most abundant fossil fuel, after coal, in the United States. Peat is of even more significance in the United States since in the contiguous 48 states, the peat deposits are generally located in areas with no significant resources of other fossil fuels. Peat deposits generally occur at the ground surface, with little or no overburden, and peat has been generally harvested by cutting it from the deposit and then the peat is transported to the use site. The use of peat commercially as a fuel by direct combustion has been practice in European countries.

2. Description of the Prior Art

Peat in its original state contains about 90 percent water. In the derivation of useful products from peat problems of dewatering the peat for its utilization have been recognized, as for example in U.S. Pat. Nos. 1,143,319; 1,145,095; 1,455,728; and 3,603,643. Utilization of upgraded hydrocarbon components from peat as a fuel has been recognized, as for example, its use as a liquid emulsion fuel in U.S. Pat. No. 728,854, and production of methane in situ in a peat bog and its pressure separation from the bog mud as taught by U.S. Pat. No. 4,187,148. Recovery of resins, waxes and oils from peat by solvent extraction has been recognized by U.S. Pat. No. 2,695,838 and production of alcohol from peat recognized by U.S. Pat. No. 2,312,196. U.S. Pat. No. 3,826,308 teaches contacting fossil fuel deposits containing organic ring compounds, preferably at an in situ depth of at least 500 feet below ground surface, with an anerobic organic ring compound fermenting microorganism under anaerobic fermentation conditions to prepare an intermediate having a lowered organic ring compound content and including paraffins and organic acids. The 3,826,308 patent teaches the in situ anaerobic contacting step may preferably be carried out in the presence of hydrogen to increase the yield of normally gaseous hydrocarbons, such as methane.

The potential for production of synthetic natural gas (SNG) from peat has been previously recognized. "Peat Gasification for SNG Production", D. V. Punwani and A. M. Rader, presented at Ninth Synthetic Pipeline Gas Symposium, Oct. 31–Nov. 2, 1977, Chicago, Ill. Many of the prior art gasification processes involve thermochemical gasification of peat and therefore necessitate removal of a substantial amount of the water from the peat, resulting in less than desirable overall energy efficiencies. The biomethanation of peat is attractive since the peat can be used without dewatering as a feed stock for biomethanation, but the organic carbon conversion efficiencies are not as high as desired because up to about 50 percent of the peat is refractory to decomposition due to limiting factors for the initial degradative steps.

SUMMARY OF THE INVENTION

This invention provides a process for in situ biological beneficiation and hydraulic harvesting of organic carbonaceous material from peat which is especially advantageous in the production of liquid and/or gaseous hydrocarbon fuel from peat. The process of this invention provides for the hydraulic removal of only the fermentation products, hydrolysis products and materials leached from the peat which are amenable to biological or chemical action leaving in situ the peat components most refractory to biological or chemical action. This avoids a major portion of waste disposal problems previously encountered with utilization of peat and provides beneficiated organic carbonaceous material for improved biological conversion to hydrocarbon fuel. The process of this invention does not require dewatering of the material removed from the peat deposit and therefore, provides considerable energy savings over many prior processes. The controlled hydraulic removal of the above materials from peat deposits provides control of flow of liquids from the peat deposit providing a managed peat deposit with reduced pollution of surrounding areas.

In the process of this invention, peat is contacted in situ with aqueous solution comprising hydrolysis promoting agent forming an active hydrolysis zone for hydrolyzing carbonaceous components of the peat to produce hydrolysis products. The formed hydrolysis products are passed from the hydrolysis zone to an active fermentation zone in situ in the peat deposit to produce fermentation products. The produced fermentation products, remaining hydrolysis products and organic carbonaceous materials leached from the peat by the aqueous solution are passed from the peat deposit to a biological or chemical process for conversion to gaseous or liquid fuel by a process accepting feeds having high water contents. Gaseous or liquid hydrocarbon fuel or a mixture of gaseous and liquid hydrocarbon fuel is produced under controlled conditions in one embodiment in an active biological reactor. In one preferred embodiment, the nutrient containing effluent of the biological reactor is aerated to add oxygen and recycled to the hydrolysis zone of the peat deposit.

It is an object of this invention to provide a process having high overall energy efficiency for production of hydrocarbon fuel from peat.

It is another object of this invention to conduct hydrolysis of the carbonaceous components of peat in situ to provide for improved removal of the carbonaceous components of peat from the peat deposit and to simultaneously provide beneficiation of the carbonaceous material for improved conversion efficiency by fermentation or methanogenic digestion for production of hydrocarbon liquid or gaseous fuels or mixtures thereof.

It is yet another object of this invention to provide a process having reduced requirements for conventional energy intense, physical-chemical pretreatment of peat prior to fermentation or aerobic biodigestion of the carbonaceous components of peat to produce hydrocarbon fuels.

It is still another object of this invention to provide a process for removal of a high proportion of the organic carbon components of peat which are susceptible to bioconversion to hydrocarbon fuels, while leaving in the peat deposit, those portions of peat most recalcitrant to biodigestion.

It is another object of this invention to provide a process for hydraulic recovery of organic carbonaceous material from a peat deposit resulting in reduced pollution to areas surrounding the peat deposit and to provide peat deposit management.

Further objects and features of the invention will become more apparent from reading of the following description of preferred embodiments of this invention.

DESCRIPTION OF THE PREFERRED EMBODIMENTS

Peat in situ in a peat deposit is a very porous structure comprising about 90 percent water. The natural peat deposits are also generally located at or near the surface of the earth so that liquid can be introduced either at the surface or subsurface at one point and withdrawn at a second location removed from the introductory point, causing general passage of liquid through the peat deposit from the introductory point to the withdrawal point.

In accordance with the present invention, an aqueous solution of a hydrolysis promoting agent is introduced into the peat deposit to create a hydrolysis zone in the peat deposit. Organic carbon components of the peat are hydrolized to compounds more susceptible to further chemical or biological action in the preparation of hydrocarbon liquid or gaseous fuels. Principal hydrolysis products include amino acids, organic acids and sugars.

Water which is high in dissolved molecular oxygen as a hydrolysis agent and desired aerobic nutrients may be introduced to a peat deposit by surface spraying or sub-surface distribution pipes at one end of a volume of the peat bog which becomes an in situ active aerobic zone. The water may be high in dissolved oxygen or oxygen may be supplied to the peat bog by bubbling it through the introductory pipes. The introduced aqueous solution may comprise active aerobic microorganisms and nutrients for the aerobic microorganisms. Suitable active aerobic microorganism systems include those known to the art as described in Microbial Ecology, Martin Alexander, published by John Wiley & Sons, Inc., New York City (1971), and Principles of Microbial Ecology, Thomas D. Brock, published by Prentice-Hall, Inc., Englewood Cliffs, N.J. (1966). Nutrients for aerobic microorganisms include nitrogen, phosphorous and trace elements. Particularly suitable for introduction is aerated waste water from sewage treatment plants, lake or river water, or recycled effluent from the biological reactor utilized in this invention to convert carbonaceous materials removed from the peat to gaseous or liquid hydrocarbon fuels. Introduction of the high oxygen content material will create an aerobic zone near the point of introduction where the metabolism of aerobic microorganisms will actively effect hydrolysis of the carbonaceous components of peat. Oxygen concentration desirable for aerobic action is greater than about 2 mg/liter dissolved oxygen up to the saturation level of about 10 mg/liter. Preferably, dissolved oxygen content in the aerobic zone is about 4 to 8 mg/liter.

Another hydrolysis promoting agent suitable for use in the process of this invention is an acid which is non-inhibitory to desired microorganisms for fermentation. Aqueous solutions of acids may be introduced into the peat deposit to form an active hydrolysis zone having a pH of about 1 to 5. Suitable acids include hydrochloric and sulfuric acids.

Another hydrolysis promoting agent suitable for use in the process of this invention is a base which is non-inhibitory to desired microorganisms for fermentation. Aqueous solutions of basic materials may be introduced into the peat deposit to form an active hydrolysis zone having a pH of about 9 to 11. Suitable bases include sodium hydroxide and calcium hydroxide.

The retention time in the hydrolysis zone is sufficient for substantial conversion of organic carbonaceous components of peat to hydrolysis products. The retention time is controlled by the flow rate of the aqueous solutions into and out of the hydrolysis zone and the size of the hydrolysis zone.

When the hydrolysis zone is aerobic, the aerobic microorganism action will reduce the oxygen content in the peat deposit creating an anaerobic environment. An anaerobic microorganism system as known to the art and typically as described in Microbial Ecology and Principles of Microbial Ecology references referred to above, will then become dominant and create an active fermentation zone. Likewise, when hydrolysis is achieved by either high or low pH environment, the lack of oxygen will cause an anaerobic system to become dominant and the microorganisms present will create an active fermentation zone of anaerobic microorganisms.

The active fermentation zone in situ in the peat deposit produces fermentation products such as low molecular weight organic acids and alcohols from the hydrolysis products produced in the hydrolysis zone. The aqueous solution also contains carbonaceous material leached from the peat, both over the long time of the contact of the water with the in situ peat and during the passage of the aqueous solution through the in situ active hydrolysis zone some of which will be converted to fermentation products in the fermentation zone.

The retention time in the fermentation zone is sufficient for substantial conversion of hydrolysis products and leached carbonaceous material to fermentation products which provide more readily gasifiable or liquefiable liquid feedstock for biological or chemical conversion processes to gaseous or liquid hydrocarbon fuels. The retention time in the fermentation zone is less than that necessary for substantial hydrocarbon gas production, such as methane. The retention time is controlled by the liquid flow rate through the fermentation zone, the size of the fermentation zone and the concentration of anaerobic microorganisms.

A collection system of pipes or channels may be readily placed at the desired distance in the peat deposit from the points of hydrolysis agent introduction. The most effective distances can be readily ascertained by consideration of the rate of flow of aqueous solution into and out of the peat deposit, the desired retention time in the hydrolysis zone and desired retention time in the fermentation zone. It is thus seen that the carbonaceous material beneficiated for further biological or chemical action to produce gaseous or liquid hydrocarbon fuels may be readily removed from the peat deposit by hydraulic means leaving in the peat deposit the portion of the peat recalcitrant to biological or chemical conversion to useful hydrocarbon fuels.

When the active in situ hydrolysis zone becomes depleted, the introduction of aqueous solution containing hydrolysis agent may be moved to the point in the peat deposit which was formerly the end of that hydrolysis zone and likewise, the point for withdrawal from the fermentation zone may be extended a like distance and the process repeated. In similar fashion, an entire peat deposit may have its biodegradable carbonaceous materials removed by hydraulic means in a manner which increases the useful organic carbon recovery from peat in a beneficiated form for further biological action in an active biological or chemical reactor to produce gaseous and/or liquid hydrocarbon fuels under controlled biological or chemical reactor conditions. The entire peat deposit may be under treatment at one time, that is, introduction of the aqueous solution of hydrolysis promoting agent at one end of the peat deposit and withdrawal of fermentation products from the other end of the peat deposit providing a fully managed peat deposit. Management of the peat deposit in this fashion prevents usual pollution of surrounding areas by overflow and draining of ground water containing contaminants from the peat deposit to surrounding areas.

The fermentation products, remaining hydrolysis products and organic carbonaceous materials leached from the peat are removed from the peat deposit and may be biologically converted to gas or liquid fuels by anaerobic production of methane, by fermentation to principally produce alcohol containing fuels or by any other biological conversion to useful gas or liquid fuels. The fermentation products, remaining hydrolysis products and organic carbonaceous materials leached from the peat may also be subjected to any suitable chemical conversions to produce desired gaseous or liquid fuels by processes accepting high water content feed. The in situ hydrolysis and fermentation provides beneficiated organic carbon materials for these processes resulting in higher organic carbon conversions by these processes to useful gaseous and liquid fuels.

For production of methane any active methane producing mesophilic or thermophilic anaerobic digestion system may be used. Methane-producing anaerobic systems utilizing acid forming bacteria and methane-producing organisms as well known to be employed to produce methane from sewage sludge can be employed in practice of the present invention. A review of the microbiology of anaerobic digestion is set forth in Biogenesis of Methane, R. A. Mah, D. M Ward, L. Baresi and T. L. Glass, Ann. Rev. Microbiol. 31, pgs. 309–341 (1977), the contents of which is incorporated in its entirety herein by reference. It is usually preferred to use mixed cultures to obtain the most complete fermentation action. Nutritional balance and pH adjustments may be made to the digester system as is known to the art to optimize methane production from the culture used.

The fermentation products, remaining hydrolysis products and organic carbonaceous materials leached from the peat in situ may be fermented under conditions which are presently known or become available to the art. Fermentation may be carried out at temperatures of about 10° to 65° C., generally at about 20° to 40° C.; retention times in excess of about ½ day and usually about ½ to 8 days; and loading rates; pretreatment of feed; fermentation reactor mixing, recycling, batch and continuous processes as known to the art for fermentation and pointed out more particularly in the references identified. Pretreatment of the feed by methods such as enzymatic or acid hydrolysis may be necessary to produce sugars for fermentation. Many such pretreatments have been developed as described by M. C. Flickinger, Current Biological Research in the Conversion of Cellulosic Carbohydrates into Liquid Fuels, Biotechnology and Bioengineering, Vol. 22, Suppl. 1, pp. 27–48 (1980). The fermentation of the sugars to alcohols is well developed in industry and described in the literature Annual Report of Fermentation Processes, D. Purlman and G. T. Tsao, Academic Press, New York, N.Y. (1978). The organic carbonaceous material withdrawn from the peat deposit in liquid form has already been subjected to pretreatment and fermentation and therefore, the conversion of organic carbon materials may be done more readily by the controlled fermentation step.

Chemical conversion to useful fuels may be utilized, such as, organic acids produced by the acid phase of anaerobic digestion may be extracted from the digestion broth and converted to liquid hydrocarbon fuels by Kolbe electrolysis as described in Liquid Fuel Production from Biomass, Sanderson, J. E., Martinez, D. V. G., Dillion, J. J., George, G. J. and Wise, D. L., 3rd Annual Biomass Energy Systems Conference Proceedings, pgs. 97–102, October, 1979, Golden, Colo.

EXAMPLE

A peat bog of 7660 acres which is exposed to the surface is sprayed by conventional spray irrigation techniques with 100 million gallons per day of aerated aqueous spray derived from 80 million gallons recycled process solution and 20 million gallons secondary waste water treatment plant effluent. This amounts to an application rate of 0.3 gallons per square foot per day. Under these conditions, the evaporative losses are about 20 percent. Hydrolysis of the organic carbonaceous components of the peat is promoted by oxygen carried by the aerated aqueous spray and is performed by aerobic and facultative anaerobic microorganisms, including bacteria and fungi. The sewage effluent serves as an inoculum containing these organisms. Aerobic metabolic activity in the peat bog results in rapid depletion of molecular oxygen creating an anaerobic environment where facultative and strict anaerobic bacteria effect conversion of the hydrolysis products to fermentation products, including organic acids and alcohols. A short hydraulic residence time of 1 to 2 days in the bog prevents further metabolism of these compounds to methane.

Aqueous solution containing hydrolysis products, fermentation products and organic carbonaceous materials leached from the peat are pumped from the bog at the rate of 100 million gallons per day. The organic carbonaceous, hydrolysis products and fermentation products concentration is 300 milligrams per liter. These materials are collected in collection pipes at the end of the fermentation zone in the peat bog and pumped to an active anaerobic methanogenic digester removed from the bog and operated under controlled conditions. Several anaerobic digesters operated in parallel are used for conversion to methane. Up-flow expanded bed type digesters are used with a hydraulic residence time of 0.5 days and temperature maintained at 35° C. resulting in methane yield of 6 SCF/lb. VS added, organic reduction rate of 75 percent and total methane production of $20 \times 10^6$ SCF/day. Effluent from the digesters is recycled to the peat bog as described above. The digester product gas contains 65 mole percent methane, 35 mole percent carbon dioxide and traces of hydrogen sulfide which is purified and upgraded by conventional techniques to SNG.

Production on the above basis can be continued in the same peat bog for about 15 to 17 years before depletion of the peat bog.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A process for production of gaseous or liquid hydrocarbon fuel from peat comprising:
   introducing an aqueous solution comprising hydrolysis promotion agent to a first zone of a natural peat deposit in situ at or near the surface of the earth and passing said aqueous solution through said first zone contacting said peat in said deposit forming in situ an active hydrolysis zone and hydrolyzing organic carbonaceous components of said peat to produce hydrolysis products;
   passing said hydrolysis products and organic carbonaceous materials leached from said peat by said aqueous solution from said hydrolysis zone to a second zone adjacent said hydrolysis zone of said natural peat deposit forming in situ an active fermentation zone and fermenting a portion of said hydrolysis products to produce liquid fermentation products;
   passing said liquid fermentation products, remaining hydrolysis products and organic carbonaceous materials leached from said peat by said aqueous solution out of said fermentation zone and out of said natural peat deposit by hydraulic means to an ex situ process for conversion to hydrocarbon fuel; and
   converting said liquid fermentation products, remaining hydrolysis products and organic carbonaceous materials leached from said peat to said gaseous or liquid hydrocarbon fuel by conversion in a biological or chemical process accepting feeds having high water content.

2. The process of claim 1 wherein said hydrolysis promoting agent is oxygen which forms an active aerobic zone thereby hydrolyzing organic carbonaceous components of said peat.

3. The process of claim 2 wherein the oxygen concentration in said active aerobic zone is maintained at about 2 to 10 milligrams per liter dissolved oxygen.

4. The process of claim 1 wherein said hydrolysis promoting agent is an acidic material which is non-inhibitory to desired microorganisms for said active fermentation zone and forms an active hydrolysis zone having a pH of about 1 to 5 hydrolyzing organic carbonaceous components of said peat.

5. The process of claim 4 wherein said acidic material is selected from the group consisting of hydrochloric acid and sulfuric acid.

6. The process of claim 1 wherein said hydrolysis promoting agent is a basic material which is non-inhibitory to desired microorganisms for said active fermentation zone and forms an active hydrolysis zone having a pH of about 9 to 11 hydrolyzing organic carbonaceous components of said peat.

7. The process of claim 6 wherein said basic material is selected from the group consisting of sodium hydroxide and calcium hydroxide.

8. In a process for production of hydrocarbon liquid fuel comprising alcohol from peat by fermentation, the improvement comprising the steps:
   introducing an aqueous solution comprising hydrolysis promotion agent to a first zone of a natural peat deposit in situ at or near the surface of the earth and passing said aqueous solution through said first zone contacting said peat in said deposit forming in situ an active hydrolysis zone and hydrolyzing organic carbonaceous components of said peat to produce hydrolysis products;
   passing said hydrolysis products and organic carbonaceous materials leached from said peat by said aqueous solution from said hydrolysis zone to a second zone adjacent said hydrolysis zone of said natural peat deposit forming in situ an active fermentation zone and fermenting a portion of said hydrolysis products to produce liquid fermentation products;
   passing said liquid fermentation products, remaining hydrolysis products and organic carbonaceous materials leached from said peat by said aqueous solution out of said fermentation zone and out of said natural peat deposit by hydraulic means to an ex situ active alcohol producing fermentation digester.

9. The process of claim 8 wherein said hydrolysis promoting agent is oxygen which forms an active aerobic zone thereby hydrolyzing organic carbonaceous components of said peat.

10. The process of claim 9 wherein the oxygen concentration in said active aerobic zone is maintained at about 2 to 10 milligrams per liter dissolved oxygen.

11. The process of claim 8 wherein said hydrolysis promoting agent is an acidic material which is non-inhibitory to desired microorganisms for said active fermentation zone and forms an active hydrolysis zone having a pH of about 1 to 5 hydrolyzing organic carbonaceous components of said peat.

12. The process of claim 11 wherein said acidic material is selected from the group consisting of hydrochloric acid and sulfuric acid.

13. The process of claim 8 wherein said hydrolysis promoting agent is a basic material which is non-inhibitory to desired microorganisms for said active fermentation zone and forms an active hydrolysis zone having a pH of about 9 to 11 hydrolyzing organic carbonaceous components of said peat.

14. The process of claim 13 wherein said basic material is selected from the group consisting of sodium hydroxide and calcium hydroxide.

15. A process for in situ conversion of organic carbonaceous material in a peat deposit to hydrolysis products, liquid fermentation products, and leached organic carbonaceous materials which are amenable to biological or chemical action to produce gaseous or liquid hydrocarbon fuels and hydraulic harvesting said hydrolysis products, liquid fermentation products and leached organic carbonaceous material from said peat deposit comprising:
  introducing an aqueous solution comprising hydrolysis promotion agent to a first zone of a natural peat deposit in situ at or near the surface of the earth and passing said aqueous solution through said first zone thereby contacting said peat in said deposit and forming in situ an active hydrolysis zone and hydrolyzing organic carbonaceous components of said peat to produce hydrolysis products;
  passing said hydrolysis products and organic carbonaceous materials leached from said peat by said aqueous solution from said hydrolysis zone to a second zone adjacent said hydrolysis zone of said natural peat deposit and forming in situ an active fermentation zone and fermenting a portion of said hydrolysis products to produce liquid fermentation products; and
  passing said liquid fermentation products, remaining hydrolysis products and organic carbonaceous materials leached from said peat by said aqueous solution out of said fermentation zone and out of said natural peat deposit by hydraulic means to an ex situ active methanogenic anaerobic digester to produce a hydrocarbon gaseous fuel.

16. The process of claim 15 wherein said hydrolysis promoting agent is oxygen which forms an active aerobic zone thereby hydrolyzing organic carbonaceous components of said peat.

17. The process of claim 16 wherein the oxygen concentration in said active aerobic zone is maintained at about 2 to 10 milligrams per liter dissolved oxygen.

18. The process of claim 15 wherein said hydrolysis promoting agent is an acidic material which is non-inhibitory to desired microorganisms for said active fermentation zone and forms an active hydrolysis zone having a pH of about 2 to 5 hydrolyzing organic carbonaceous components of said peat.

19. The process of claim 18 wherein said acidic material is selected from the group consisting of hydrochloric acid and sulfuric acid.

20. The process of claim 15 wherein said hydrolysis promoting agent is a basic material which is non-inhibitory to desired microorganisms for said active fermentation zone and forms an active hydrolysis zone having a pH of about 9 to 11 hydrolyzing organic carbonaceous components of said peat.

21. The process of claim 20 wherein said basic material is selected from the group consisting of sodium hydroxide and calcium hydroxide.

22. A process for in situ conversion of organic carbonaceous material in a peat deposit to hydrolysis products, liquid fermentation products, and leached organic carbonaceous materials which are amenable to biological or chemical action to produce gaseous or liquid hydrocarbon fuels and hydraulic harvesting said hydrolysis products, liquid fermentation products and leached organic carbonaceous material from said peat deposit comprising:
  introducing an aqueous solution comprising hydrolysis promotion agent to a first zone of a natural peat deposit in situ at or near the surface of the earth and passing said aqueous solution through said first zone and contacting said peat in said deposit thereby forming in situ an active hydrolysis zone and hydrolyzing organic carbonaceous components of said peat to produce hydrolysis products;
  passing said hydrolysis products and organic carbonaceous materials leached from said peat by said aqueous solution from said hydrolysis zone to a second zone adjacent said hydrolysis zone of said natural peat deposit and forming in situ an active fermentation zone and fermenting a portion of said hydrolysis products contained therein to produce liquid fermentation products; and
  passing said liquid fermentation products remaining hydrolysis products and organic carbonaceous materials leached from said peat by said aqueous solution out of said fermentation zone and out of said natural in situ peat deposit by hydraulic means.

23. The process of claim 22 wherein said hydrolysis promoting agent is oxygen which forms an active aerobic zone thereby hydrolyzing organic carbonaceous components of said peat.

24. The process of claim 23 wherein the oxygen concentration in said active aerobic zone is maintained at about 2 to 10 milligrams per liter dissolved oxygen.

25. The process of claim 22 wherein said hydrolysis promoting agent is an acidic material which is non-inhibitory to desired microorganisms for said active fermentation zone and forms an active hydrolysis zone having a pH of about 1 to 5 hydrolyzing organic carbonaceous components of said peat.

26. The process of claim 25 wherein said acidic material is selected from the group consisting of hydrochloric acid and sulfuric acid.

27. The process of claim 22 wherein said hydrolysis promoting agent is a basic material which is non-inhibitory to desired microorganisms for said active fermentation zone and forms an active hydrolysis zone having a pH of about 9 to 11 hydrolyzing organic carbonaceous components of said peat.

28. The process of claim 27 wherein said basic material is selected from the group consisting of sodium hydroxide and calcium hydroxide.

* * * * *